United States Patent [19]

Frigerio et al.

[11] Patent Number: 4,931,038

[45] Date of Patent: Jun. 5, 1990

[54] COMPLEX OF PRODUCTS FOR THE RAPID AND NOT-INVASIVE TREATMENT OF BILIARY CALCULOSIS

[75] Inventors: Giuliano Frigerio, Milan; Aldo Roda, Bologna; Enrico Roda, Bologna, all of Italy

[73] Assignee: Gipharmex S.p.A., Milan, Italy

[21] Appl. No.: 127,456

[22] Filed: Dec. 2, 1987

[30] Foreign Application Priority Data

Dec. 5, 1986 [IT] Italy ............................ 22596 A/86

[51] Int. Cl.$^5$ ........................ A61H 23/00; A61B 17/22
[52] U.S. Cl. ............................... 604/22; 128/24 A
[58] Field of Search .................... 604/22; 260/397.1; 128/24

[56] References Cited

U.S. PATENT DOCUMENTS

| | | | |
|---|---|---|---|
| 3,433,226 | 3/1969 | Boyd | 128/24 A |
| 3,565,062 | 2/1971 | Kuris | 128/24 A |
| 4,439,366 | 3/1984 | Scolostico et al. | 260/397.1 |
| 4,440,688 | 3/1984 | Scolastico et al. | 260/397.1 |
| 4,755,167 | 7/1988 | Thistle et al. | 604/22 |
| 4,787,371 | 11/1988 | Grasser et al. | 128/24 A |

OTHER PUBLICATIONS

*Merck Index,* 9th Ed, 1976, p. 258, "Chenodeoxy–Cholic Acid".

*Primary Examiner*—C. Fred Rosenbaum
*Attorney, Agent, or Firm*—Neuman, Williams, Anderson & Olson

[57] ABSTRACT

The present invention relates to a complex of products useful for the not-invasive and rapid treatment of the biliary calculosis of cholesterolic nature. It is based upon the coupling of a special apparatus generating medium-energy or medium-low-energy ultrasounds with pharmaceutical compositions based on biliary acids, capable of de-saturating bile super-saturated with cholesterol.

13 Claims, No Drawings

COMPLEX OF PRODUCTS FOR THE RAPID AND NOT-INVASIVE TREATMENT OF BILIARY CALCULOSIS

Biliary calculosis is a widely diffused pathologic condition which arises from a metabolic error at liver level, an error which essentially results in the production of lithogenous bile, i.e., a bile supersaturated in cholesterol. This production of lithogenous bile leads to, along with the cooperation of other factors, the precipitation of cholesterol crystals and to the formation of calculi.

The true epidemiological dimension of biliary lithiasic disease has been long underestimated, however recent data indicates that at least 15% of adult population is affected by such a disease, even if in most cases it is disregarded, in an much as it can develop in a completely asymptomatic way. The management of the biliary calculosis was, until to approximately ten years ago, or exclusively surgical competence; the advent in therapy of the biliary acids capable of de-saturating the lithogenous bile opened new therapeutical possibilities, in that they made it possible the dissolution to be obtained by medical way, even if by very long-lasting treatments (of from 6 months up to 2 years), of the already formed biliary cholesterol calculi.

The main impediment to the medical treatment by such biliary acids has been the excessively long duration of the treatment, even when it has been suitably used in the indicated. Said long duration causes frequently the missed respect by the patient of the prescription and also, in the long term, the possible arising, over time, of situations hindering the same dissolution of the calculus, such as, e.g., the deposition of calcareous concretions on calculus surface, such to delay or prevent the dissolving thereof.

More recent attempts to obtain an ultra-rapid dissolving of the calculi (in a few minutes or hours) were carried out by adopting means of invasive type: the local perfusion, by probes or catheters, of chemical solvents of ether type, the application of shock waves, and so forth. These are approaches which are still now at an experimental level, and which shall anyway remain limited to highly specialized Centres.

For the solution of the problem, the present invention proposes a complex of products for the rapid, not-invasive treatment of the biliary calculosis of cholesterolic nature, characterized in that it comprises a pharmaceutical composition containing, as its active principle, a biliary acid capable of desaturating bile supersaturated in cholesterol, and a device generating medium-power or medium-low-power ultrasounds.

These are a complex of products which propose a treatment for the dissolution of the biliary calculi, having essential characteristics of not-invasiveness and of rapid achieving of the dissolution, by "rapidity" the reduction down to a few months (from 1 to 3 months) of the many months normally required for the medical treatment with the above mentioned biliary acids being understood.

The complex of products of the present invention is constituted by:

pharmaceutical compositions with biliary acids of the type definable as biliary acids capable of desaturating, by different mechanisms, bile supersaturated in cholesterol; examples thereof are represented by chenodeoxycholic acid and ursodeoxycholic acid, but without limitations in this regard, in that more recently other biliary acids have shown to have analogous properties, and in a near future they will probably find similar clinic applications;

special apparatuses, capable of producing low-energy and/or medium-energy ultrasounds, and of focusing their energy on the seats containing the calculary concretions (calculi in cholecyst) without altering, not even to a minimum extent, the surrounding tissues.

It is known that low-energy or very low-energy ultrasound apparatuses have been long used for diagnostic purposes, and constitute a very valuable aid in various specialistic fields (cardiology, obstetrics, gastroenterology, and so forth), as well as very high-energy apparatuses are used for "aimed" applications, capable of "hitting" very well circumscribed seats, to destroy particular tissues or formations.

The present invention relates, on the contrary, to the use of medium-low-energy apparatuses, i.e., devices with powers comprised within the range of from 2-3 milliwatts/cm$^2$ of application surface area, applied by pulsed emissions each thousandth of second, up to powers of the order of 2-4 watts/cm$^2$ of application surface area, applied by emissions pulsed up to one every each thousandth of second. Such apparatuses are purposely prearranged for modifying and accelerating the rate of dissolution of the calculus in the complex system represented by the solid crystal of cholesterol inside the phospholipids-biliary acids-cholesterol medium, wherein the concentration of cholesterol has been decreased to levels of absolute or relative undersaturation, thanks to the effect of continuous oral administration by way of one of the above mentioned biliary acids; the special apparatus of the invention can be optionally, but not necessarily, equipped with a suitable and precise aiming system, which is capable of identifying the application focus, and of concentrating the application beam as efficaciously as possible.

Within the range of energy power envisaged by the present invention, at least two types of devices can be defined, one of which operates at a lower energy level for longer applications, and/or repeated applications at an out-patient and private level, and the other, operating at a higher energy level, and with a possible incorporated aiming system, is destined to shorter applications, and/or applications more spaced in time, to be carried out at specialistic Centres.

For the purpose of better understanding the characteristics and the advantages of the invention, hereunder some examples of practical embodiment, which are not to be understood as being limitative of the same invention, are supplied.

EXAMPLE 1

A patient with three radiotransparent calculi of medium size, in operating cholecystis, recognized by echography and subsequent cholecystography. A treatment with chenodeoxycholic acid at the dosage rate of 15 mg/kg daily is established; in as much as the treatment is carried out on a subject of 80 kg, 5 capsules of 250 mg are administered daily. After 1 week of treatment with CDCA, a first 1-minute-long application of medium-energy ultrasound apparatus is carried out at a specialized Centre. The treatment with CDCA is continued, and regular weekly applications, always 1 minute long, are carried out with the ultrasound device. After 2 weeks of treatment with CDCA, the daily dosage is slightly reduced (4 capsules daily) due to the occurrence of a minor diarrhoea, but, after a further week, it is possible to return back to the initial dosage rate without any particular problems.

The echographic checks are carried out with a regular two-weekly frequency, to monitor the beginning of a possible dissolution of the calculi. After two months, an evident partial dissolution of the calculi, and after four months a complete dissolution thereof, is observed.

EXAMPLE 2

A patient with five radiotransparent calculi of medium and small sizes, in operating cholecystis, diagnosed by echography and subsequent cholecystography. A treatment with ursodeoxycholic acid at the dosage rate of 8 mg/kg daily is established; in as much as the treatment is carried out on a subject of 75 kg, 2 capsules of 300 mg are administered daily. After 2 weeks of treatment with UDCA, a daily application, of a duration of approximately 3 minutes each, of the medium-low-energy ultrasound apparatus is prescribed. The treatment with UDCA is continued, and regular daily applications, always approximately 3 minutes long, are carried with the medium-low-energy ultrasound apparatus.

The echographic checks are carried out with a regular two-weekly frequency, to monitor the proceeding of the calculus dissolution process. After 1 month, an evident partial dissolution of the calculi, and after two months the complete dissolution thereof, is observed.

In general, it can be observed that a particularly relevant aspect of the present invention is represented by the fact that such apparatuses, within the provided energy range, are not capable of causing, per se, the disintegration of the biliary calculi, and, furthermore, that the biliary acids which can be used for dissolution purposes, when used as such, cause the dissolution of the biliary calculi susceptible of medical treatment in percentages of the order of from 30 to 50% of cases, and anyway require at least 6–12 months of administration; the combination of biliary acid administration with the periodical applications of the ultra-sound apparatus according to the invention causes, on the contrary, the dissolution of cholesterol biliary calculi in slightly larger percentages of cases, but, above all, in considerably shorter times (of from 1 to 3 months); therefore, a surprising "synergistic action" between the components of the complex of the present invention is evident.

We claim:

1. A therapeutic system for the rapid and not-invasive treatment of biliary calculosis of cholesterolic nature and accompanying concentrations of calculi, comprising a pharmaceutical composition containing, as its active principle, a biliary acid capable of desaturating bile super-saturated in cholesterol, in combination with a low-power or medium-power ultrasound generating apparatus which generates low-energy or medium energy ultrasounds, said ultrasounds being focused on said calculi concentrations, wherein said combination of said biliary acid and said ultrasound functions to cause the efficient dissolution of said calculi concentrations.

2. A therapeutic system according to claim 1, wherein said ultrasound generating apparatus has a power output within the range of from 2 milliwatts/cm$^2$ of application surface area, to 4 watts/cm$^2$ of application surface area, said power output being applied to emissions pulsated every thousandth of second.

3. A therapeutic system according to claim 1, wherein said ultrasound generating apparatus is equipped with an aiming device to define the focus of application of said ultrasounds on said calculi concentrations.

4. A therapeutic system for the rapid and not invasive treatment of biliary calculosis of cholesterolic nature and accompanying concentrations of calculi, characterized in that it comprises a biliary acid, and low-energy or medium-energy ultrasounds at a dosage sufficient to cause complete dissolution of said calculi concentrations.

5. A therapeutic system according to claim 1, wherein said biliary acid and said ultrasounds are periodically applied, at successive times, after each other to cause complete dissolution of said calculi concentrations.

6. A therapeutic system according to claim 1, wherein said biliary acid and said ultrasounds are periodically applied according to a prearranged sequence sufficient to cause complete dissolution of said calculi concentrations.

7. A therapeutic system according to claim 1, wherein said biliary acid and said ultrasounds are periodically applied, simultaneously to each other sufficient to cause complete dissolution of said calculi concentrations.

8. A method for the rapid and not-invasive treatment of biliary calculosis comprising:
   administering a pharmaceutical composition containing as its active principle, a biliary acid capable of de-saturating bile super-saturated in cholesterol to a patient having biliary calculosis and accompanying concentrations of calculi; and
   subjecting said calculi concentrations to a dosage of low-energy or medium-energy ultrasounds sufficient to cause dissolution of said calculi concentrations, wherein said biliary acid and said ultrasound function in combination to cause the efficient dissolution of said calculi concentrations.

9. A method for the rapid and not-invasive and not-invasive treatment of biliary calculosis as claimed in claim 11, wherein said biliary acid and said ultrasounds are applied at successive intervals, after each other, sufficient to cause complete dissolution of said calculi concentrations.

10. A method for the rapid and not-invasive treatment of biliary calculosis as claimed in claim 8, wherein said biliary acid and said ultrasounds are periodically applied according to a prearranged sequence sufficient to cause complete dissolution of said calculi concentrations.

11. A method for the rapid and not-invasive treatment of biliary calculosis as claimed in claim 8, wherein said biliary acid and said ultrasounds are periodically applied simultaneously to each other sufficient to cause complete dissolution of said calculi concentrations.

12. A therapeutic system for the rapid and not-invasive treatment of biliary calculosis of cholesterolic nature and accompanying concentrations of calculi, comprising a pharmaceutical composition containing, as its active principle, a biliary acid capable of de-saturating bile super-saturated in cholesterol, selected from the group consisting of chenodeoxycholic acid and ursodeoxycholic acid, in combination with a low-power or medium-power ultrasound generating apparatus which generates low-energy or medium-energy ultrasounds, said ultrasounds being focused on said calculi concentrations, wherein said combination of said biliary acid and said ultrasounds function to cause the efficient dissolution of said calculi concentrations.

13. A method for the rapid and not-invasive treatment of biliary calculosis comprising:
   administering a pharmaceutical composition containing as its active principle, a biliary acid capable of de-saturating bile super-saturated in cholesterol, selected from the group consisting of chenodeoxycholic acid and ursodeoxycholic acid, to a patient having biliary calculosis and accompanying concentrations of calculi; and
   subjecting said calculi concentrations to a dosage of low-energy or medium energy ultrasounds sufficient to cause the efficient dissolution of said calculi concentrations, wherein said biliary acid and said ultrasound function in combination to cause the efficient dissolution of said calculi concentrations.

* * * * *